(12) United States Patent
Krill et al.

(10) Patent No.: US 6,239,294 B1
(45) Date of Patent: May 29, 2001

(54) PROCESS TO PRODUCE α-TOCOPHEROL-ACETATE

(75) Inventors: Steffen Krill, Speyer; Stephan Kretz, Beibergemünd; Klaus Huthmacher, Gelnhausen, all of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/571,314

(22) Filed: May 15, 2000

(30) Foreign Application Priority Data

Mar. 9, 2000 (DE) .............................................. 100 11 402

(51) Int. Cl.$^7$ .................................................. C07D 311/04
(52) U.S. Cl. .............................................................. 549/408
(58) Field of Search ............................................... 549/408

(56) References Cited

U.S. PATENT DOCUMENTS 3,789,086 * 1/1974 Frick et al. ........................ 260/345.5
5,523,420 * 6/1996 Lowack et al. ....................... 549/411

* cited by examiner

*Primary Examiner*—Amelia Owens
(74) *Attorney, Agent, or Firm*—Smith, Gambrell & Russell, LLP

(57) ABSTRACT

Process for the production of α-tocopherol acetate in a recycling process by condensation of trimethylhydroquinone diesters and isophytol in the presence of a catalyst system consisting of a zinc halide and of an aqueous protonic acid and optionally of an elemental metal in a polar solvent/water mixture which is extractable or miscible with water and subsequent recycling of the catalyst system.

7 Claims, No Drawings

PROCESS TO PRODUCE α-TOCOPHEROL-ACETATE

DESCRIPTION

The present invention relates to a new recycling process for the production of α-tocopherol acetate by condensation of trimethylhydroquinone diesters and isophytol in the presence of a catalyst system consisting of a zinc halide (Lewis acid) and of an aqueous protonic acid (Bronsted acid) and optionally of an elemental metal in a polar solvent/water mixture which is extractable or miscible in water, and subsequent recycling of the catalyst system.

α-Tocopherol and its derivatives are of importance as feed additives, as antioxidants, as agents for stimulating the blood circulation, as agents for retarding cell ageing and for related applications. In particular, pulverulent formulations of alpha-tocopherol acetate (vitamin E acetate) together with a suitable silica are established on the market for use as feed additives.

Most well-known are processes for producing α-DL-tocopherol, that is, the unesterified, light-sensitive vitamin E form which is not stable in storage. In these processes, alpha-tocopherol is first of all prepared by condensation of trimethylhydroquinone with isophytol, with condensation of water, and in a separate step is esterified with stoichiometric quantities of an acylating agent to form the vitamin E acetate. This procedure is outlined in the following diagram:

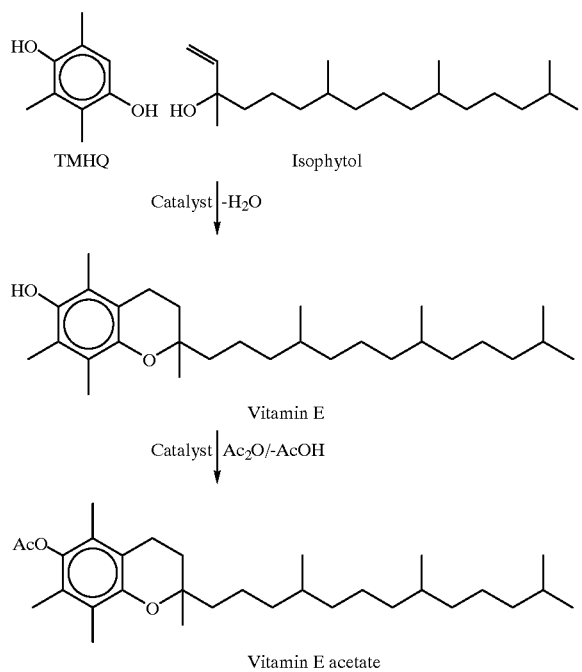

According to this prior art one generally commences from trimethylhydroquinone (TMHQ), which is reacted with isophytol using various catalyst systems. (DE-OS 4243464 (=U.S. Pat. No. 5,523,420,) DE-OS 19603142, EP 0694 541, DE 196 03 142, EP (0 949 255 A1).

On conclusion of the reaction, the product must subsequently be completely acetylated in order, for example, to obtain the usual commercial vitamin E acetate which is stable in storage. Common to all these processes is the fact that that they do not lead directly to tocopherol acetate, the usual commercial form of Vitamin E which is stable in storage.

There have also been attempts to react isophytol with trimethylhydroquinone esters as educt of the synthesis of tocopherols.

The main advantage of using the corresponding trimethylhydroquinone ester, for example, trimethylhydroquinone diacetate (TMHQ-DA), as the synthetic equivalent of TMHQ is that the acetyl group present in the vitamin E acetate end product is already present in the TMHQ-DA educt molecule and, by skilful control of the reaction, vitamin E acetate is attained directly by condensation of TMHQ-DA with isophytol, without the necessity of having subsequently to esterify with stoichiometric or even hyperstoichiometric quantities of acetic anhydride in a separate reaction step. Up to the present, however, there has been found no economic process which allows the condensation of the trimethylhydroquinone di- or monoesters used as educt with isophytol to be carried out with sufficiently high yields and vitamin E acetate to be obtained directly.

FR-A 2 259822 (DE-OS 2 404621) relates to the use of diacetylated trimethylhydroquinone TMHQ-DA. But the condensation with isophytol in the presence of a solid acid described in that document delivers a yield of only approximately 41% α-DL-tocopherol (vitamin E) and does not lead to the corresponding esters.

The condensation of trimethylhydroquinone monoacetate (TMHQ-MA) with isophytol is described in DE-OS 2 160 103 (=U.S. Pat. No. 3,789,086). With the use of Fe (II) $Cl_2$ and hydrochloric acid and simultaneous removal of the water of reaction, only small quantities of α-tocopherol acetate are obtained and it is necessary to acetylate subsequently with amine catalysis and addition of hyperstoichiometric quantities of acetic anhydride. The yields are unsatisfactory, the two-step procedure is expensive and the necessity of reacting with hyperstoichiometric quantities of acetic anhydride to obtain vitamin E acetate entails a high consumption of chemicals. The working-up of the catalyst phase obtained after the reaction is not dealt with.

According to JP-OS 51-80859 (Jul. 15, 1976), trimethyl-hydroquinone or its esters are reacted with isophytol in the presence of zinc chloride. The reaction leads to α-tocopherol at temperatures of more than 100° C., in accordance with the set object.

A disadvantage of this process, which is quite economic as regards the yields achieved, is the problem of waste water which arises owing to the use of large quantities of zinc chloride. A simple recycling of these aqueous zinc chloride solutions obtained after extraction is not possible as, in the case of the condensation of TMHQ, in addition to the water required for the extraction, further water of reaction, which deactivates the catalyst solution, is formed during the reaction. (see Bull. Chem. Soc. Japan., 68, (1995), 3569 ff and Bull. Chem. Soc. Japan., 69, (1996), 137). Attempts to recycle the zinc halide phase extracted with water (approx. 20–60 wt. % $ZnCl_2$) and to reuse it for the condensation result in a lowering of the reaction yield and in a poorer quality of product. In the Patent Application EP 0 850 937 A1, the reaction is carried out in a solvent which is immiscible or only slightly miscible with water, after the reaction the catalyst phase is extracted with water and, after concentration of the aqueous phase to about 60–90%, the catalyst solution thus obtained is returned to the reaction at 20–200° C. A disadvantage in this procedure is the fact that the zinc halide mixtures are in the form of a mash at room temperature and hence can only be delivered by pumps specifically intended for this field of application. To obtain a liquid form of catalyst, the mash has to be concurrently heated to an appropriate temperature, which likewise requires a considerable expense and is thus uneconomic.

A considerable disadvantage of this process is the high volatility of the protonic acid required for the reaction, in particular HCl during the removal of water by distillation in order to concentrate the Zn chloride solutions. Owing to this loss, in each case the quantity of HCl has to be added in the next batch, which complicates the process.

With regard to the yields, the hitherto most efficient process for the reaction of TMHQ-DA is described in DE-OS 197 57 124.7, in which a binary catalyst system consisting of a zinc halide and a protonic acid is used in various inert, aprotic solvents such as, for example, acetic ester or aromatics (toluene). Here the working-up is carried out by aqueous extraction of the entire catalyst phase after the condensation, a mixture of α-tocopherol together with α-tocopherol acetate being present in the product phase. In this procedure, for the subsequent esterification of the α-tocopherol it is in addition necessary to add a catalyst for the acetylation and likewise to remove it again by aqueous extraction after the reaction. Where ester-containing solvents are used, the presence of water during the reaction gives rise to the further problem that, in addition to the saponification of the TMHQ-DA taking place in situ, there is also the resulting partial saponification of the solvent. In this way the ester used as solvent yields the corresponding organic acids and alcohols, which have to be removed from the product by means of expensive separation processes or accumulate in the recycling process during the return of the solvent.

2,3,5-trimethylhydroquinone diesters are prepared in known manner from ketoisophorone (4-oxoisophorone= KIP) in the presence of an acid catalyst and of an acylating agent such as carboxylic anhydride (in the simplest case, acetic anhydride with release of acetic acid) or acyl halides. The relevant processes are documented in several patent specifications (for example, DE 2 149 159, EP 0 808 815 A2, EP 0 850 910 A1, EP 0 916 642 A1). The formation of the TMHQ-DA conventionally used for the synthesis of vitamin E acetate in all cases takes place in the presence of an acid catalyst or a mixture of several suitable acids under appropriate conditions. On conclusion of the reaction, a mixture comprising TMHQ-DA, a few aromatic secondary products, in the main trimethyl catechol diester and trimethylphenol derivatives, excess acylating agent, the catalyst and acetic acid is obtained. This mixture has to be worked up in order to separate off the TMHQ-DA used as educt for the condensation with isophytol; in the simplest case an adequate TMHQ-DA quality is obtained by crystallisation from this acetic acid solution. The product isolated by this procedure still has an acetic acid content of up to 50 wt. %, depending on the degree of purification.

In the processes representative of prior art which are described above, the working-up of the catalyst solutions used in the reaction is not dealt with.

The object of the invention is to provide an improved process for the production of (α-tocopherol esters in a recycling process, in which in the first step the reaction already proceeds as far as possible in the direction of the ester and to regenerate the catalyst phase obtained in the reaction after working-up in such a way that it can easily be returned to the reaction without lowering of the catalytic activity. In particular, the object of the invention was to find a process which makes it possible to recycle the solution of active catalyst in a (liquid) form which is easily metered and can be handled well even at room temperature, without resulting lower yields or a deterioration of the product quality owing to reuse of the catalyst solution.

In this connection, a process is also to be found which permits the catalyst component used, in particular even the protonic acid, to be returned after the catalyst regeneration, thus avoiding the necessity of a complete fresh replenishment of this component.

Another object of the invention was to find a process whereby it is also possible to use an acetic TMHQ-DA, such as is obtained in the synthesis commencing from KIP as raw product.

The invention relates to a process for the production of alpha-tocopherol acetate by condensation of trimethylhydroquinone diacetate (TMHQ-DA) and isophytol (IP) at moderate temperatures in the presence of a catalyst system consisting of a zinc halide and of a protonic acid and optionally of an elemental metal, in particular zinc, in acetic acid as solvent, wherein, after the condensation reaction, the mixture of tocopherol/tocopherol acetate obtained after the condensation is subsequently acetylated at moderate temperatures in the presence of the condensation catalyst, which remains in the organic phase after the condensation after the acetic catalyst phase has been removed, with regeneration and recycling of an aqueous acetic catalyst solution. In particular the chlorides and bromides, and also mixtures of these components, are used as zinc halide catalyst. The basic chlorides and bromides of zinc, that is, the corresponding oxy- and hydroxyhalides, are also active catalysts of the process according to the invention.

Vitamin E acetate is obtained by using TMHQ-DA as the equivalent of TMHQ and reacting it directly with isophytol. Only a partial subsequent acetylation is necessary, and not an equimolar subsequent acetylation, as the product mixture obtained after the reaction contains only a little vitamin E in addition to the main product vitamin E acetate.

In this connection, the use of acetic acid as solvent allows vitamin E acetate to be obtained in crude yields of >96% and, besides isolated TMHQ-DA, acetic TMHQ-DA (accessible as crude product from the synthesis of TMHQ-DA ex KIP) may also be used as the aromatic component.

The bulk of the catalyst can be separated after the condensation reaction by simple phase separation of the acetic acid phase (catalyst phase I) from the vitamin E/vitamin E acetate phase (product phase I), with an adequate concentration of catalyst still remaining in the organic phase to allow a mild, highly selective subsequent acetylation at moderate temperatures. After the acetylation, the vitamin E acetate phase is freed from the remains of the catalyst by aqueous extraction and the aqueous catalyst phase obtained (catalyst phase III) is combined with the catalyst phase I (II) obtained after the condensation. In the simplest case, this catalyst phase is worked up by separating a mixture of acetic acid and water by distillation, without the transfer over of the active catalyst component in the distillate. An acetic, aqueous concentrated catalyst solution remains, the catalyst phase IV, which can be reused for the condensation.

This catalyst solution is also liquid at room temperature and is an ideal formulation of the active catalyst, which is easy to handle and meter at moderate temperatures.

The use of acetic acid as preferred solvent and extracting agent for the catalyst solution makes it possible to recycle the catalyst solution in the form of an easily handled, aqueous acetic solution which, by simple distillation from acetic acid and water, can be regenerated in such a way that none of the catalytically active components is lost with the distillate and the catalyst solution obtained can again be returned to the reaction without loss of activity.

An embodiment of the process appears as follows in the simplified block flow diagram:

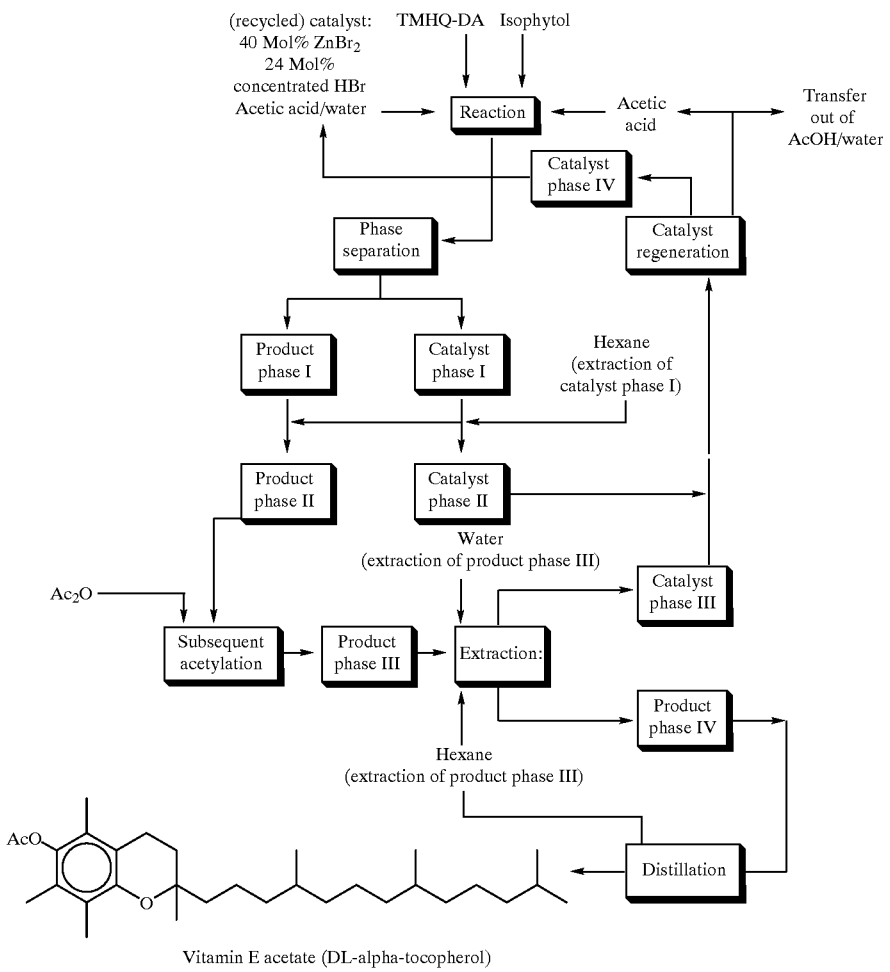

Vitamin E acetate (DL-alpha-tocopherol)

The condensation of the aromatic structural entity TMHQ-DA with isophytol in the presence of the catalyst system 5 consisting of $ZnX_2$ and HY (X=halide, hydroxide, oxide; Y–anion of a Brønsted acid) and optionally of an elemental metal, in particular zinc, added as the third catalyst component, proceeds with excellent yields if the reaction is carried out for the most part in a protonic solvent which is extractable or miscible with water, in particular acetic acid, and the catalyst solution used for the condensation and subsequent acetylation is introduced into the reaction in the form of an aqueous acetic solution of $ZnX_2$ and HY, in particular hydrogen chloride and hydrobromic acid.

The reaction of the components used as educt in acetic acid produces excellent yields. Compared with the esters conventionally used as solvents for the condensation, acetic acid has the advantage that it is inert under the reaction conditions, whereas corresponding esters have a tendency to hydrolyse in the presence of the acid catalysts and water.

At this point, the process involving the use of TMHQ diesters as the synthetic equivalent of TMHQ differs considerably, as usually (in the TMHQ process) the water is removed as an azeotrope with the solvent during the reaction and thus cannot enter into reaction with esters used as solvents. Where TMHQ-DA is used, however, a saponification of the diester must take place in situ, so that the corresponding monoester of TMHQ can be formed as an intermediate, because only the phenolic hydroxyl function is available as a reactive group for the condensation with isophytol.

The acetic acid can be added fresh to each batch. In a preferred variant, the acetic acid recovered as secondary product during the acetylation with acetic anhydride in an initial batch is used as solvent. A further portion of the acetic acid enters the reaction through the use of crude, undried TMHQ-DA from the production of TMHQ-DA ex KIP and acetic anhydride.

The concentration of acetic acid can be approximately 10 to 300 wt. %, with reference to the TMHQ-DA used, the best results usually being obtained at 50 to 150 wt. % acetic acid, with reference to TMHQ-DA.

The quantity of water in the reaction mixture is adjusted to a concentration of $10^{-2}$–200 Mol % with reference to TMHQ-DA, the quantity of water being found from the total of the content of the recycled aqueous acetic catalyst phase and the freshly replenished aqueous HY (catalyst-protonic acid). In the main, the concentration of water in the reaction mixture is determined via the water content of the recycled catalyst phase.

The condensation reaction is carried out in the presence of the catalyst components $ZnX_2$-HY and optionally of an elemental metal in acetic acid as solvent at temperatures of between 0° C. and 150° C., the best results being obtained within a temperature range of 40° C. to 80° C. The subsequent acetylation is carried out in the presence of the catalyst components $ZnX_2$-HY and optionally of an elemental metal at temperatures of between −20° C. and 100° C., the best results being obtained at 0 to 40° C.

Suitable Lewis acids, according to the patent literature DE 197 57 124 A1, are zinc salts, in particular the halides such as zinc chloride and zinc bromide, the corresponding hydroxides formed under reaction conditions also being included in this term. The required quantities of the Lewis acids, based on the TMHQ-DA used, are 10 Mol %–200 Mol %, in particular 20 Mol %–50 Mol %. In the main, in the recycling process the concentration of the Lewis acid is adjusted via the Lewis-acid content of the aqueous acetic recycling solution during recycling of the regenerated catalyst solutions.

The Lewis acid need not be introduced into the reaction in the form of the purchasable component, but can be produced in situ by mixing corresponding quantities of hydrohalic acid with the corresponding metal, in particular zinc. After regeneration of the catalyst solution, the corresponding zinc halide can be almost entirely detected again, deficient quantities are compensated for by fresh replenishment of the elemental metal and an aqueous hydrohalic acid up to the required concentration level.

According to the patent literature DE 197 57 124 A1, hydrohalic acids in concentrated form or in the form of their aqueous solutions can be used as protonic acids. Good results are achieved with the use of hydrogen bromide in particular. However, sulfuric acids [sic], sulfuric acid/$SO_3$ mixtures with various $SO_3$-concentrations and superacids having an $H_0$-value of less than −11.9, such as, for example, the perfluoroalkanoic acids, or else mixtures of boric acid and oxalic acid are also suitable. The required quantities of the protonic acids, based on the TMHQ-DA used, is 0.01 Mol %–100 Mol %, in particular 5 Mol %–50 Mol %.

In the main, in the recycling process the concentration of the protonic acid is adjusted via the protonic-acid content of the aqueous acetic recycling solution during recycling of the regenerated catalyst solutions.

The required quantities of the elemental metal used, based on the TMHQ-DA used, are 0.01 Mol %–100 Mol %, in particular 1 Mol %–50 Mol %.

The sequence of the educt-/catalyst addition is optional up to isophytol, which is finally added to the mixture of the remaining components.

In a preferred embodiment, initially the acetic acid used as solvent is placed in a reactor (for example, acetic acid from TMHQ-DA production, or from a previous batch of the vitamin E acetate production after the acylation with acetic anhydride, or as fresh solvent) and in it are dissolved the catalyst component, the aqueous hydrohalic acid and the corresponding zinc halide and optionally elemental zinc. TMHQ-DA is added to this solution. The suspension thus obtained is brought to reaction temperature (approx. 60° C.). Isophytol, optionally in the form of acetic acid solution, is added to this mixture over a period of 2–6 hours. At the end of the reaction, the reaction mixture is cooled to room temperature; two defined phases are formed, the catalyst phase (catalyst phase I) and the product phase (product phase I).

The lower, heavy phase contains vitamin E/vitamin E acetate as a minor constituent and consists mainly of an aqueous acetic solution of the catalyst component. The proportion of product components (vitamin E and vitamin E acetate) in the catalyst phase I is about 0.1–5 Mol %, usually 0.5–2 Mol %, of the total quantity of product formed. The proportion of product contained in the catalyst phase can be recovered by simple extraction with a suitable solvent and is then combined with the upper product phase. Through suitable control of the reaction, the quantity of product in the catalyst phase is so small that an extraction can be dispensed with.

The upper phase (product phase I) contains traces of the catalyst components $ZnX_2$ and HY and, as the major constituent, a mixture of vitamin E and vitamin E acetate. Depending on the control of the reaction, the proportion of vitamin E to vitamin E acetate varies within the range of 1:1 and 1:10; the ratio obtained after the condensation is usually approximately 1:3. Above all, the water concentration in the reaction solution and the temperature of the reaction can be identified as conditions determining the ratio of vitamin E to vitamin E acetate.

The quantity of catalyst remaining in the upper product phase is sufficient for the acetylation at moderate temperatures of the quantity of unesterified vitamin E which is present in addition to the vitamin E acetate.

After the phase separation of catalyst phase I from the product phase I, the proportion of product components, which make up about 0.1–5 Mol % of the total quantity of product formed, is removed from the catalyst phase by extraction. At this point, all suitable solvents which are immiscible or only slightly miscible with the catalyst phase can be used as extracting agent, in particular aliphatic, cycloaliphatic or aromatic solvents. Examples which may be given are pentane, hexane, heptane, octane, nonane, [sic] decalin, ligroin, petroleum ether, cyclohexane, benzene, toluene, xylene, or else halogenated derivatives of the above-mentioned solvents. Other common solvents such as esters, in particular carbonate esters and aliphatic carboxylic esters, and aliphatic alcohols as well as mixtures of the above-mentioned groups of solvents are suitable for this extraction.

The extraction proceeds very efficiently even with small quantities of aliphatic extracting agents, the quantity of extracting agent being variable within ranges of between 1 wt. % and 100 wt. %, based on the catalyst phase I being extracted.

The extracted phase, which consists substantially of vitamin E/vitamin E acetate and the extracting agent, is combined with the product phase I, so that altogether there is one resulting phase, the product phase II, which is composed of the product phase I, which contains the major part of the vitamin E and vitamin E acetate formed. 95–99.1% of the whole of the vitamin E +vitamin E acetate formed after the condensation reaction is found in this phase and the extract of the catalyst phase I, which contains 0.1–5% of the whole of the vitamin E and vitamin E acetate formed.

In another embodiment, likewise according to the invention, the extraction of the catalyst phase I can be circumvented by adding the extracting agent, prior to the phase separation, to the reaction solution obtained after the condensation. In this way the product phase I obtained after the phase separation can with success be virtually completely freed from water, which would interfere with the subsequent acylation. The acylation is then carried out in the extracting agent under suitable conditions, without appreciably influencing the reaction rate and selectivity of the reaction.

A further advantage of adding the extracting agent prior to the first phase separation is the fact that only negligible quantities of vitamin E and vitamin E acetate are present in the catalyst phase I obtained after phase separation. In this way, the extraction of the catalyst phase I in order to obtain these residual quantities of useful material can thus be dispensed with.

The subsequent acetylation can be carried out batchwise or continuously, the product phase II being composed of acetic acid, the extracting agent, vitamin E and vitamin E acetate. The residual water concentration present in the phase to be acylated is optionally eliminated by the addition of a corresponding excess of acetic anhydride with the formation of acetic acid, which in any case is present in the reaction system from the beginning. In an advantageous embodiment, acetic anhydride is added to the product phase II, the reaction being efficiently catalysed even at room temperature owing to the presence of the catalyst system consisting of protonic acid/Lewis acid. Depending on the control of the reaction and the concentration of the catalyst components, the reaction can take place within a temperature range of between −20° C. and 100° C., preferably between 0° C. and 40° C.

The reaction takes its course and gives rise to the product phase III, which contains vitamin E only in a concentration of <1% relative to vitamin E acetate. In order to work up this product phase, in a subsequent step a catalyst extraction with water and optionally a cosolvent, in particular methanol or ethanol, is carried out, a solvent which is immiscible or only slightly miscible with water being used simultaneously to assist the phase separation, in order to remove traces of product from the aqueous acetic catalyst phase II thus obtained.

Regarding the selection of the extracting agent for the organic product phase III or the catalyst phase III, the criteria which apply are the same as those already stated in the case of the extraction of the catalyst phase I. A procedure wherein the extraction of the catalyst phase I and the extraction of the catalyst phase II are carried out in the same extracting agent is particularly preferred. It is particularly advantageous to carry out this separation of product (vitamin E acetate) and catalyst ($ZnX_2$-HY) as an (optionally) multistep countercurrent extraction.

After extraction of the product phase III with water and optionally with a cosolvent such as methanol or ethanol, an aqueous acetic phase containing the catalyst components, the catalyst phase III, is obtained. This catalyst phase III, which contain [sic] the catalysts of the acylation, is combined with the catalyst phase II obtained after the condensation. The result of this is an aqueous acetic catalyst phase, which contains quantitatively the active catalyst component $ZnX_2$ and a major part of the active catalyst component HY.

This catalyst phase is treated by means of appropriate technical procedures in such a way that a phase containing the catalyst components, the catalyst phase IV, is obtained. After replenishment of the partially consumed component HY, this catalyst phase IV can be reused for the condensation of the structural entities TMHQ-DA and isophytol. The catalyst regeneration in the main comprises the partial removal of acetic acid and/or water, with substantially the catalyst components $ZnX_2$ and HY remaining in a concentrated water/acetic acid solution. In the simplest case, for this purpose a distillation of the combined catalyst phases II and III is carried out, with water and acetic acid being obtained as distillate, without the transfer over of a concentrated aqueous solution of HY in the distillate.

The distillation and the associated regeneration of the catalyst phase is carried out at a pressure of 0.1 torr to 760 torr. The regeneration of the combined catalyst phases II and III by distillation is carried out, depending on the established pressure, within a temperature range of 20° C.–200° C. The possibility of carrying out the catalyst regeneration at reduced pressure and correspondingly moderate temperatures affords additional advantages with regard to the choice of the material of the equipment used. In another variant according to the invention, the catalyst regeneration is carried out by concentrating the combined catalyst phases II and III to small volume in such a way that, besides water and acetic acid, HY is also partially removed by distillation. It is then necessary to replenish the resulting catalyst phase IV with the corresponding concentration of HY in order to maintain the full catalytic activity.

The regeneration of the combined catalyst phase can also be effected by alternative methods apart from the distillation methods described, in particular the separation of water and/or acetic acid by separation by means of a suitable membrane. In this variant the active catalyst solution is concentrated by selective removal of acetic acid and/or water, likewise leaving a catalyst solution IV which, in addition to an acetic acid-water concentration as given above, also contains an active catalyst component. In another variant of the procedure, 0.1 wt. %–5 wt. % of the corresponding mineral acid HY can be added to the extracting medium (consisting of water and a cosolvent such as methanol or ethanol) in order to ensure a complete extraction of the catalyst component from the product phase III.

Even with repeated recycling, the catalyst solutions IV obtained by the described procedure are sufficiently viscous within a temperature range of 0° C.–200° C. to be delivered in the liquid state by means of suitable pumps, without the resulting crystallisation of the catalyst components, which would necessitate additional measures for the recycling.

The procedure according to the invention for carrying out the condensation of TMHQ-DA with isophytol in acetic acid as solvent and the described procedure for regenerating the catalyst solution as aqueous acetic acid-containing $ZnX_2$-HY containing catalyst solution provide an uncomplicated, efficient process for the direct production of vitamin E acetate, which renders possible a constant catalytic activity in the catalyst used, without or with only negligible replenishment of the catalyst component HY.

Through the procedure according to the invention for carrying out the production of vitamin E acetate ex TMHQ-DA and isophytol, a solution/catalyst matrix has successfully been found which makes it possible, by using a water-soluble solvent which can be extracted with water, in particular acetic acid, to achieve a selective product preparation after condensation and renders possible a catalyst separation of the condensation catalyst from the product phase obtained, consisting of vitamin E/vitamin E acetate and acetic acid. Moreover, after the catalyst separation of the vitamin E/vitamin E acetate phase an adequate catalyst concentration for the subsequent acylation with a suitable acylating agent at moderate temperatures is made possible and, after acylation with a suitable acylating agent with the formation of the product vitamin E acetate, an extraction of the catalyst phase with an aqueous extracting agent is carried out and by regeneration of the catalyst phase thus obtained, with removal of water/acetic acid, an active catalyst phase IV which is easy to handle at moderate temperatures is obtained and can be employed for repeated use as a catalyst solution, without loss of activity.

The following Examples illustrate the process according to the invention. The content of the mixtures obtained after condensation and the content of the products were determined quantitatively by analysis of the products compared with available commercial preparations (Fluka: 98.5% vit. E Ac).

EXAMPLES

Example 1

112.6 g $ZnBr_2$, 300 ml (315 g) glacial acetic acid and 50.6 g hydrobromic acid 48% were placed in a 2 l four-necked flask and then 300.1 g TMHQ-DA was introduced, with stirring. After a brief flushing with nitrogen at room temperature, the reaction mixture was heated to 60° C. over a period of 10 minutes. The isophytol was then added over 4 hours at 60° C. and subsequently stirred for 1 hour at 60° C.

After the mixture had been cooled to room temperature, the two phases were separated and the catalyst phase I was washed twice with 50 ml n-hexane. The n-hexane extracts were combined with the product phase I to form product phase II. To this was then added, over a period of 45 minutes, an at least stoichiometric quantity of acetic anhydride in such a way that the reaction temperature did not exceed 22° C., and the mixture was then allowed to react for a further 15 minutes.

350 ml n-hexane and 250 ml water were then added to the black reaction solution and the whole was vigorously stirred for approximately 10 minutes. The emulsion was separated in a separatory funnel and the organic phase was washed twice with 50 ml water.

The product phase IV was concentrated to constant weight in a rotary evaporator at 60° C. and 1 mbar. The recovered n-hexane can be reused for subsequent extractions.

The two aqueous extracts (catalyst phase III) were combined with the catalyst phase II and, by means of simple distillation, comprising Liebig condenser with Claisen head, were concentrated up to a temperature at the bottom of the column of 146° C.

179.5 g of residue (violet solution) was obtained. This residue excels in that it can be pumped and handled well at room temperature.

The composition of the residue was as follows:

60–65% $ZnBr_2$

10–13% HBr

13–16% water

10–15% AcOH

This residue can be reused for the subsequent reaction without loss of yield and selectivity.

Examples 2–9

The quantities of $ZnBr_2$, HBr and ACOH shown in the Table were added to the residue obtained from Example 1. The required water content for the reaction was established by adding $Ac_2O$, but could also be regulated through the separation of acetic acid and water during the recycling of the catalyst. It is evident that no loss of activity occurs even after the acetic acid catalyst phase has been recycled eight times.

| | | | | Zinc bromide | | | HBr 48% | | |
|---|---|---|---|---|---|---|---|---|---|
| | TMHQ-DA | Isophytol | | [g] | [g] | total | [g] | [g] | total |
| Ex. | [g] mMol | [g] mMol | Mol % | rec. mMol | fresh mMol | [g] mMol | rec. mMol | fresh mMol | [g] mMol |
| 1 | 300.1 | 395.1 | 105 | — | 112.6 | 112.6 | — | 50.56 | 24.27 |
| | 1250 | 1313 | | — | 500 | 500 | — | 300 | 300 |
| 2 | 300.1 | 395.1 | 105 | 105.4 | 7.2 | 112.6 | 19.89 | 9.12 | 24.27 |
| | 1250 | 1313 | | 468.0 | 32.0 | 500 | 245.9 | 54.1 | 300 |
| 3 | 300.1 | 395.1 | 105 | 106.1 | 6.5 | 112.6 | 19.50 | 9.91 | 24.27 |
| | 1250 | 1313 | | 471.0 | 28.9 | 500 | 241.2 | 58.8 | 300 |
| 4 | 300.1 | 395.1 | 105 | 106.9 | 5.7 | 112.6 | 19.64 | 4.64 | 24.27 |
| | 1250 | 1313 | | 474.7 | 25.3 | 500 | 242.8 | 57.2 | 300 |
| 5 | 300.1 | 395.1 | 105 | 106.7 | 5.9 | 112.6 | 19.4 | 10.25 | 24.27 |
| | 1250 | 1313 | | 473.7 | 26.2 | 500 | 239.2 | 60.8 | 300 |
| 6 | 300.1 | 395.1 | 105 | 109.6 | 3.0 | 112.6 | 21.4 | 6.0 | 24.27 |
| | 1250 | 1313 | | 486.7 | 13.3 | 500 | 264.6 | 35.6 | 300 |
| 7 | 300.1 | 395.1 | 105 | 106.6 | 6.0 | 112.6 | 21.6 | 5.6 | 24.27 |
| | 1250 | 1313 | | 473.4 | 16.6 | 500 | 266.8 | 33.2 | 300 |
| 8 | 300.1 | 395.1 | 105 | 103.7 | 8.9 | 112.6 | 19.5 | 9.8 | 24.27 |
| | 1250 | 1313 | | 460.3 | 39.5 | 500 | 241.4 | 58.6 | 300 |
| 9 | 300.1 | 395.1 | 105 | 110.1 | 2.48 | 112.6 | 21.1 | 6.56 | 24.27 |
| | 1250 | 1313 | | 489.0 | 11.0 | 500 | 261.1 | 38.9 | 300 |

| | $H_2O$ | | | $AC_2O$ | | Tocopherol phase | | Yield |
|---|---|---|---|---|---|---|---|---|
| | [g] rec. | total [g] | $AC_2O$ [g] | NaAc [g] | [g] weighed | (HPLC) % E | | % theor. |
| Ex. | mMol | mMol | mMol | mMol | out | % EAc | mmEAc | TMHQ-DA |
| 1 | — | 26.29 | — | 92.8 | 827.5 | 20.1 | 386.2 | 97.0 |
| | — | 1459.4 | — | 890.7 | | 46.6 | 815.8 | |
| 2 | 26.1 | 22.52 | 48.13 | 91.8 | 847.7 | 18.4 | 362.1 | 97.0 |
| | 1448.5 | 1250 | 462.0 | 881.4 | | 46.7 | 837.5 | |
| 3 | 24.8 | 26.29 | 21.1 | 93.5 | 848.0 | 19.6 | 385.9 | 97.5 |
| | 1375.0 | 1459.4 | 202.7 | 897.7 | | 45.9 | 823.4 | |

-continued

| | | | | | | | | |
|---|---|---|---|---|---|---|---|---|
| 4 | 25.6 | 26.29 | 24.93 | 94.0 | 847.7 | 19.8 | 389.7 | 97.7 |
| | 1419.7 | 1459.4 | 239.3 | 902.5 | | 45.9 | 823.1 | |
| 5 | 23.5 | 26.29 | 14.61 | 90.4 | 836.6 | 18.5 | 359.3 | 97.4 |
| | 1304.7 | 1459.4 | 140.3 | 867.6 | | 47.7 | 844.9 | |
| 6 | 27.16 | 26.29 | 22.54 | 92.9 | 858.6 | 18.7 | 372.8 | 97.4 |
| | 1507.9 | 1459.4 | 220.8 | 891.8 | | 45.9 | 833.7 | |
| 7 | 29.96 | 26.29 | 38.0 | 92.4 | 848.8 | 18.6 | 366.6 | 97.0 |
| | 1663.3 | 1459.4 | 364.7 | 886.9 | | 46.5 | 835.0 | |
| 8 | 27.92 | 26.29 | 39.1 | 92.5 | 859.6 | 18.4 | 367.2 | 96.3 |
| | 1550 | 1459.4 | 375 | 887.4 | | 45.4 | 825.6 | |
| 9 | 26.8 | 26.29 | 22.61 | 93.1 | 849.8 | 19.2 | 378.8 | 98.6 |
| | 1487.5 | 1459.5 | 217 | 894.1 | | 46.6 | 837.8 | |

Examples 10–12

The procedure was as in Example 1 and the catalyst was recycled as in Examples 2–9, but in addition 3.27 g Zn (4 Mol % based on TMHQ-DA) was added with the respective TMHQ-DA. This has the advantage that a crude vitamin E acetate with a greater colour purity is obtained and an expensive replenishment of $ZnBr_2$ can be avoided and the replenishment of the lacking zinc bromide can be compensated for by in situ formation commencing from aqueous HBr and Zn.

| | TMHQ-DA | Isophytol | | Zinc bromide | | | | Zn | | HBr 48% | | |
|---|---|---|---|---|---|---|---|---|---|---|---|---|
| | | | | rec. | fresh | total | | | | rec. | fresh | total |
| Ex | [g] mMol | [g] mMol | Mol % | [g] mMol | [g] mMol | [g] mMol | Mol % | [g] mMol | Mol % | [g] mMol | [g] mMol | [g] mMol |
| 10 | 300.1 | 395.1 | 105 | — | 112.6 | 112.6 | 40 | 3.27 | 4 | — | 50.56 | 24.27 |
| | 1250 | 1313 | | — | 500 | 500 | | 50 | | — | 300 | 300 |
| 11 | 300.1 | 395.1 | 105 | 116.5 | — | 116.5 | 41.4 | 3.27 | 4 | 13.71 | 21.99 | 24.27 |
| | 1250 | 1313 | | 517.5 | — | 517.5 | | 50 | | 169.5 | 130.5 | 300 |
| 12 | 300.1 | 395.1 | 105 | 124.6 | — | 124.6 | 44.3 | 3.27 | 4 | 13.8 | 21.91 | 24.27 |
| | 1250 | 1313 | | 553.2 | — | 553.2 | | 50 | | 170.0 | 130 | 300 |

| | $H_2O$ | | | | Tocopherol phase | | | Yield |
|---|---|---|---|---|---|---|---|---|
| | [g] rec. | total [g] | $AC_2O$* [g] | $AC_2O$** [g] | [g] weighed | (HPLC) % E | mmE | % theor. |
| Ex | mMol | mMol | mMol | mMol | out | % EAc | mmEAc | TMHQ-DA |
| 10 | — | 26.29 | — | 82.9 | 852.1 | 14.1 | 279.0 | 97.6 |
| | — | 1459.4 | — | 796.0 | | 51.7 | 932.0 | |
| 11 | 29.51 | 26.29 | 84.62 | 86.4 | 887.5 | 14.3 | 294.7 | 98.5 |
| | 16.38 | 1459.5 | 812.3 | 829.3 | | 49.3 | 952.6 | |
| 12 | 28.1 | 26.29 | 76.3 | 86.6 | 889.1 | 14.3 | 295.2 | 97.2 |
| | 1560.1 | 1459.5 | 732.3 | 831.0 | | 48.2 | 906.6 | |

What is claimed is:

1. A process for the production of α-tocopherol acetate in a recycling process comprising condensating a trimethylhydroquinone diester and isophytol in a reaction in the presence of a catalyst mixture comprising a zinc halide and an aqueous protonic acid and optionally an elemental metal in a polar solvent/water mixture which is extractable or miscible with water to obtain a mixture of α-tocopherol and α-tocopherol ester
   i) esterifying the obtained mixture of α-tocopherol and α-tocopherol ester with an acylating agent,
   ii) recovering by aqueous extraction a solution of catalyst and regenerating and returning a solution containing acetic acid to the reaction and
   iii) concentrating the catalyst mixture of zinc halide and protonic acid and recycling the resulting concentrate in liquid form into the reaction.

2. A process as claimed in claim 1, wherein the zinc halide is a member selected from the group consisting of zinc chloride, bromide, oxy- and hydroxychloride, oxy- and hydroxybromide and mixtures thereof.

3. A process as claimed in claim 1, wherein the protonic acid is hydrochloric acid and hydrobromic acid and the elemental metal is zinc.

4. A process as claimed in claim 1, wherein acetic acid is the solvent and extracting agent for the catalyst solution.

5. A process as claimed in claim 1, wherein acetic anhydride is the acylating agent.

6. A process as claimed in claim 1, wherein the aqueous acetic acid catalyst mixture is concentrated by distillation or by membrane separation.

7. A process as claimed in claim 1, wherein the reaction is carried out continuously and repeatedly recycled.

* * * * *